United States Patent [19]

Clark

[11] 4,091,035

[45] May 23, 1978

[54] PROCESS FOR THE PRODUCTION OF HYPOALLERGENIC LANOLIN

[75] Inventor: Edward Watson Clark, Bradford, England

[73] Assignee: Woolcombers Limited, Bradford, England

[21] Appl. No.: 762,133

[22] Filed: Jan. 24, 1977

[30] Foreign Application Priority Data

Feb. 5, 1976 United Kingdom ............... 04503/76

[51] Int. Cl.$^2$ ................................................ C07J 9/00

[52] U.S. Cl. ............................ 260/397.25; 260/397.2; 260/419; 568/913

[58] Field of Search ...................... 260/412.8, 419, 428, 260/428.5, 420, 643 F, 643 G, 397.25, 397.2; 424/312, 365

[56] References Cited

U.S. PATENT DOCUMENTS

| | | | |
|---|---|---|---|
| 2,758,125 | 8/1956 | Sunde | 260/428.5 |
| 3,272,850 | 9/1966 | Richey et al. | 260/428 |
| 3,853,930 | 12/1974 | Richey | 260/428 |
| 3,955,004 | 5/1976 | Strauss et al. | 260/428.5 |
| 3,983,147 | 9/1976 | Senda et al. | 260/412.8 |

*Primary Examiner*—Winston A. Douglas
*Assistant Examiner*—John F. Niebling
*Attorney, Agent, or Firm*—Norris & Bateman

[57] ABSTRACT

A process for the production of hypoallergenic lanolin by the reduction of free fatty acids and detergents by the use of a polar aliphatic alcohol such as methanol, ethanol, iso-propanol, acetone and acetic acid.

6 Claims, No Drawings

PROCESS FOR THE PRODUCTION OF HYPOALLERGENIC LANOLIN

This invention relates to improvements in lanolin and more particularly to the production of lanolin rendered hypoallergenic.

Hypoallergenic Lanolin is herein defined as lanolin so treated that it will show a significantly lower incidence of detectable allergy amongst people known to be dermatologically hypersensative to ordinary untreated lanolin.

Lanolin is the refined wax from the fleece of sheep. Lanolin is extensively used in pharmaceutical ointments and in cosmetics as a highly effective emollient for the skin with secondary value as a powerful water-in-oil emulsifier. The substance is usually produced and marketed in the form of Anhydrous Lanolin and the pharmacopoeias of most countries include a monograph specifying tests for purity and characterisation. Synonyms for the substance are Wool Fat, Wool Wax, Adeps Lanae, etc. Usually, and for present purpose, the substance is referred to as "Lanolin".

A detailed chemical analysis of lanolin has shown that the substance consists predominantly of esters and a minor proportion of fatty alcohols in the free state. Analyses carried out on more than 30 different samples of lanolin showed that free fatty alcohols were always present in amounts varying from 5% to 12.6%.

The effect of the natural free fatty alcohols in lanolin on its emulsifying power has been investigated and it has been found after removing completely the free fatty alcohols by absorption on a column of activated alumina from a solution of lanolin in light petroleum that the resultant lanolin esters had negligible emulsifying power. The yield of treated lanolin was 62%.

In general use lanolin is a substance with a long history of safety. Nevertheless there is a very small incidence of primary specific allergy to lanolin amongst the general population as there is to most substances. In the case of lanolin this incidence has been quantified at the level of 5.5 ± 4.2 per million at the most. For general purposes this may be regarded as a satisfactory low incidence but sufferers from certain types of dermatitis particularly leg ulcers become abnormally sensitive and can develop allergy to several different substances simultaneously, one of which may be lanolin. Amongst patients at skin hospitals, therefore, the incidence of allergy to lanolin tends to be higher than amongst the general population. Since lanolin is a valuable ingredient of ointment bases, some of which are used in the treatment of skin disorders, it is clearly an advantage to treat lanolin so as to reduce its allergenic potential, low though this is. It has already been shown that the allergenic constituents of lanolin lie within its total fatty alcohol content, and probably in the aliphatic alcohol constituents thereof. It is now important, however to distinguish between the total fatty alcohols of lanolin and its free fatty alcohols. Although the latter may account for up to 12% of the lanolin, the total fatty alcohols amount to more than 50% of a typical lanolin as evidenced by the total unsaponifiables varying between 50 and 54% of the original. The total fatty alcohols of lanolin are produced commercially as a valuable emulsifying agent. Their production involves the chemical breakdown of the lanolin esters by alkaline hydrolysis followed by removal of the resultant total fatty acid fraction so as to isolate the desired unsaponifiables. The fatty alcohols of lanolin are known as Wool Alcohols, Wool Wax Alcohols, Alcoholia Lanae etc.

It has now been found, firstly that the free fatty alcohols in lanolin are broadly similar in composition to the total fatty alcohols obtained by ester cleavage. Secondly and more importantly that by removing these free fatty alcohols or substantially reducing the amount present without chemical breakdown of the lanolin esters and without completely eliminating the natural water-in-oil emulsifying power of the lanolin, the incidence of allergy from the lanolin is markedly reduced. In other words, the allergic potential of lanolin lies not merely in its total alcohols as hitherto supposed, but more specifically in the relatively minor proportion of free fatty alcohols. It is important to note that according to the invention the free fatty alcohols must be removed without significant hydrolysis of the lanolin esters, so that the latter remain in the finished product in a substantially unchanged form. Removal of free fatty alcohols in this way is thus fundamentally different from those processes which are used commercially to produce the total lanolin alcohols, and which destroy the esters, and is also fundamentally different from any other processes which involve chemical modification designed to reduce the incidence of lanolin allergy, for example, the blocking of the free hydroxyl groups of lanolin by acetylation. By such processes lanolin loses its essential identity. The total fatty alcohols resulting from ester hydrolysis are not soft like lanolin but are a hard wax unsuitable for direct application to the skin and the total fatty acids of lanolin are also very different from lanolin itself, both chemically and physically and have inferior emulsifying power. Acetylated lanolin also has very inferior emulsifying properties.

In contrast to these chemically changed products, lanolin treated according to the invention retains the usual chemical and physical properties of lanolin and meets the chemical requirements of national pharmacopoeias. It thus represents a significant and important advance on products known hithereto.

A second feature of the invention is the discovery that synthetic detergent residues in lanolin increase the detectable level of incidence of allergy, over and above that which is due to the free fatty alcohols. It is known that detergents can be present in lanolin and that they can be removed by extraction with 45% isopropanol in order to improve the emulsifying power of the lanolin but the connection with lanolin allergy has not been recognised hithereto. It has now been discovered that detergent residues in lanolin, even in relatively small quantities are sufficient to increase significantly the detectable incidence of allergy, particularly when the natural free fatty alcohols of lanolin are also present in significant amount. Dermatological patch tests have been carried out at hospitals on a number of patients who were known to be hypersensitive to ordinary lanolin.

These patients were treated with four test substances:

1. ordinary, untreated lanolin
2. lanolin from which detergent has been removed
3. lanolin from which free fatty alcohols had been removed.
4. lanolin from which both detergent and free alcohols had been removed.

The number of positive reactions for hypersensitivity to these four test substances were:

Sample No: (1) 50.9%

Sample No: (2) 25.0%

Sample No: (3) 36.8%

Sample No: (4) 1.9%

These results show that, whereas removing either free fatty alcohols or detergent from lanolin markedly reduces the incidence of positive reactions, removal of both from the same lanolin effects a much greater reduction. In other words, free fatty alcohols and detergent together in lanolin appear in some way to exert a combined and more intense action than either singly.

Although it is known in the art how to remove free fatty alcohols from lanolin, it was not known that such removal would reduce the allergenicity of the lanolin. It had also been proposed to remove detergent from lanolin but it has not been known previously that such removal would reduce the allergenicity of the lanolin. We have discovered that removal of free fatty alcohols reduces allergenicity and removal of detergent also reduces allergenicity but in addition and unexpectedly that removal of both free fatty alcohols and detergent from the same lanolin results in a very great reduction in allergenicity, substantially to zero.

The present invention involves three separate but related features.

Firstly, that the free fatty alcohols of lanolin rather than the total fatty alcohols have the allergenic potential; secondly, that detergent residues in lanolin increase the level of detectable incidence of allergy; thirdly that removal of both free fatty alcohols and detergent from the same lanolin gives a combined and unexpectedly large reduction in the incidence of allergic reaction. In other words, a means of making lanolin substantially hypoallergenic has been discovered.

To put the invention into effect, any suitable method of removing free fatty alcohols from lanolin may be used, plus any suitable method of removing detergent residues.

The invention comprises a process for the production of hypoallergenic lanolin by the reduction of free fatty alcohols to less than 3.0% and of the detergent content to less than 0.05%.

It has been found that detergent residues can be removed from lanolin by adsorption on an activated earth and subsequent filtration. Examples of suitable earths are those known commercially as Fulmont 700C, or Tonsil Optimum, the adsorption being suitably carried out by stirring at 50° or 80° C for 3 to 6 hours before filtration. The activated earth may alternatively be used not directly on lanolin but on a solution of lanolin in a substantially non-polar solvent such as hexane. The use of activated earth in this way is already known in the art for the purpose of bleaching lanolin by absorbing colouring matter. Where such a system is already in operation, it therefore gives an additional benefit of removing detergent from the lanolin so that only the removal of free fatty alcohols is then necessary to put the invention into effect.

It has also been found that free fatty alcohols may be removed from lanolin by subjecting the substance to a high temperature and high vacuum as in a molecular still, thin film evaporator or wiped film evaporator. Although it is known to distil the total lanolin alcohols under vacuum for the purpose of improving their colour and odour, this is a fundamentally different process to the present invention. For instance, in distilling the total lanolin alcohols it is important for economic reasons to distil the substance as completely as possible so as to leave a minimum residue usually mounting to 10 to 20% of the feed; also the colour of the residue is relatively unimportant.

In contrast, in carrying out the invention a minimum distillate is required consistent with a sufficient reduction in the free fatty alcohols content of the lanolin. The residue, which is the principal desired fraction, amounts to 75 to 95% of the feed. It has been found impossible thus to distill off the free fatty alcohols from lanolin without accompanying loss of some of the desired esters, therefore it is important to work under such conditions as will minimize such losses. Typical conditions are a temperature of 180° to 240° C and a pressure of 20 to 150 millitorrs. It is to be noted that pressures in this region are much lower than those known in the art for the purpose of deodorising lanolin, namely 500 millitors to 100 torrs. Lower pressures according to the invention allow a lower temperature to be used, and thereby minimise thermal degradation of the lanolin being treated. Depending on the actual working conditions used and the particular feedstock, the yield of treated lanolin according to the invention is approximately 75% to 95% of the total feed.

In contrast to these two-stage methods of putting the invention into effect, it is advantageous to use a single stage system for removing at the same time both detergents and free fatty alcohols from lanolin. To achieve this, the lanolin is subjected to a series of extractions or washes with a polar lower aliphatic alcohols such as methanol, ethanol, isopropanol or n-proponol or with another polar solvent such as acetone or glacial acetic acid at a substantially higher concentration than the 45% needed for the removal of detergent only. The more concentrated the said polar solvent and the higher the temperature of treatment, the more free fatty alcohols are removed from the lanolin but with a concomitant, undesired increase in solubility of the lanolin esters. By using a concentration and temperature appropriate for each particular polar solvent, a compromise is reached whereby free fatty alcohols and detergent are simultaneously extracted from the lanolin without excessive losses of the desired lanolin esters. The preferred polar solvent is ethanol, conveniently used in the United Kingdom in the form of Industrial Methylated Spirits (IMS) at a concentration of 70% to 100% with 90% to 97% preferred. The number of washes necessary varies from approximately 5 to 30 depending upon the amount of free fatty alcohols and detergent in the original lanolin but usually 10 to 20 washes are suitable using equal volumes of lanolin and polar solvent for each wash. The temperature during washing is advantageously kept above the melting point of the lanolin so that liquid/liquid separations may be carried out, but should not be higher than necessary otherwise undesirable losses of the valuable esters can occur and ebullition can cause problems. The overall temperature range, depending upon other factors, is approximately 40° to 80° C with 45° to 65° preferred.

Instead of treating the lanolin by discrete washes with a polar solvent in the said manner, the washing may be carried out continuously in a suitable column or vessel by the passage through the lanolin of said polar solvent until the desired volumetric ratio has been reached. The feed of polar solvent may be fresh solvent throughout or the spent polar solvent issuing from the lanolin may be continuously distilled for purification and the distillate recirculated. The polar solvent feed to the lanolin is advantageously effected through a suitable dispersing device for example a perforated plate or series of such plates to break up the solvent into small drops.

In a further embodiment of the said continuous method of washing, untreated lanolin may be continuously introduced at the top of the column and polar solvent at the bottom, the two phases flowing countercurrent to each other.

Continuous counter-current washing may alternatively be carried out in any other suitable form of device designed to bring two substantially immiscible liquid phases into progressive contact with each other, such as a pulsed column.

Although a manner of examples of ways have now been described in which the invention may be carried out, these are not to be regarded as a limitation. Any suitable method of removing free fatty alcohols from lanolin, in conjunction with any suitable method of removing detergent residues from the same lanolin, either simultaneously or as separate processes, may be used to give the combined result which makes the lanolin hypoallergenic. It has been discovered that in a minority of cases lanolin may initially contain little or no synthetic detergent residues, for example, where the lanolin was obtained from crude wool grease which had resulted from washing wool otherwise than with detergent, such as by the use of ordinary soap or by organic solvents. With such lanolins only the removal of free fatty alcohols is necessary to achieve the object of the invention and this removal may be carried out by the said washing with polar solvent or said subjection to high temperature and high vacuum or by other suitable means.

If particularly low residual contents of free fatty alcohols are desired in lanolin, it is advantageous to use both washing with polar solvent and treatment with high vacuum and temperature as a 2-stage process.

In yet another embodiment of the invention the said washing with polar solvent is carried out not directly on lanolin but on a solution of lanolin in an organic solvent which is substantially non-polar and immiscible with the said polar solvent, for example, hexane or other relatively low-boiling petroleum distillate.

The present process is distinguished from the known "Neumi" process in which wool grease in hexane solution is washed with alkaline isopropanol of concentration 35.7% to 60% in order to reduce the acidity of the wool grease. This process has been found not to reduce substantially the free fatty alcohol content of lanolin for two reasons. Firstly the alcohol concentration is too dilute and secondly the alkaline conditions can cause hydrolysis of some of the lanolin esters with resultant liberation of free fatty alcohols which is the exact opposite of the objects of the invention. However by using higher concentrations from 70% to 100% of isopropanol or other appropriate polar solvent under non-alkaline conditions, the free fatty alcohol concentration in lanolin dissolved in the polar solvent can be reduced substantially in the same way as when washing the lanolin directly except that it is possible to carry out the washing at room temperature or thereabouts instead of higher. P It has also been found advantageous not to remove the free fatty alcohols completely from the lanolin. If removal is complete, the finished product has very poor water absorption power, for example down to 16% compared to 355% in the case of the original. A reduction in the free fatty alcohol content of the lanolin to approximately 3.0% or less has been found to make the lanolin substantially hypoallergenic whilst retaining moderate water adsorption power, usually in the range of 100% to 200%. This is adequate for most purposes, particularly since the resultant emulsions have good stability but in certain exceptional cases higher water absorption power may be required. In such cases it has been found that the addition to lanolin treated according to the invention of a relatively small quantity, within the approximate range of 0.5 to 3.0% of an inoccuous fatty alcohol such as cetyl alcohol, stearyl alcohol, cholesterol, sitosterol or mixtures of such fatty alcohols, will augment the water absorption power up to 200% to 300%.

Of the examples of alcohols given, stearyl alcohol is preferred because of its particularly low allergenicity and good emulsifying action. Although the addition of such fatty alcohols is petroleum jelly is known in the art as a means of importing water absorption powers and also the use of cetyl alcohol along with the total lanolin alcohols and/or lanolin in petroleum jelly is known for similar purposes, it has not been previously known to remove completely or partially the allergenic free fatty alcohols from lanolin and replace them in part with a substantially inoccuous fatty alcohol, to restore water adsorption.

Not all the free fatty alcohols of lanolin may be allergenic. There may be only one component or a few specific components thereof which provoke allergy. Nevertheless, the act of removing or reducing the free fatty alcohol content of lanolin according to the invention reduces the detectable allergenicity of the substance, especially in the absence of detergent.

Contents of free fatty alcohols in lanolin referred to here have been determined by a method in which a sample is acetylated and injected into a gas chromotograph column using OVl as the stationary phase and nitrogentas carrier gas with a flame ionisation detector. Injections of acetylated total lanolin alcohols are used as reference standard.

The following examples illustrate ways in which the invention may be carried out.

EXAMPLE 1

100 g of Anhydrous Lanolin BP were washed 10 times at 45° C with 100 ml per wash of 95% ethanol (I.M.S.) These 10 extracts were bulked and evaporated to dryness and the solid residue washed 20 times in the same manner as previously.

The two washed lanolin fractions were mixed and found to have a free fatty alcohol content of 2.1% compared to 9.0% in the original and a detergent content of 0.01% compared to 0.10% in the original. Comparison of the treated lanolin with the original on lanolin-hypersensitive patients at a skin hospital showed a reduction in incidence of lanolin allergy from 40% to zero.

EXAMPLE 2

Anhydrous lanolin BP was treated by stirring for 4 hr at 60° C with 5% of its weight of activated earth, type Fulmont 700 C, and then filtered whilst hot. The detergent content was thereby reduced from 0.12% to less than 0.01% The resultant detergent-free lanolin was then passed through a molecular still, type CVC MS 15A at 220° C and 80 millitorrs absolute pressure. The free alcohols were thereby reduced from 8.7 to 2.2%. The overall yield of finished product after all treatment was 81%. Testing the resultant treated product on hospital patients previously found to be hypersensitive to ordinary lanolin showed a reduction in incidence of allergy from 89.47% to 5% at one hospital and from 23% to zero at a second hospital on different patients.

EXAMPLE 3

Anhydrous Lanolin BP was washed continuously in a column containing perforated dispersing plates by passing through it 20 times its volume of 95% ethanol (IMS) at 50° C and then dried. The yield of finished product was 79% of the feed and the residual free fatty alcohol and detergent contents were 1.8% and 0.01% compared to 7.3% and 0.28% respectively in the original. The washing reduced the water absorption of the lanolin from 180% to 130% and the incorporation of 2% of cholesterol into the washed lanolin augmented the water absorption to 200%.

EXAMPLE 4

15 g of lanolin as used in Example 3 were dissolved in 85 ml of hexane and the solution washed 8 times at room temperature with 50 ml per time of 93 I.M.S. After distilling solvent from the lanolin the treated sample had contents of free fatty alcohols and detergent reduced to 2.1% and 0.03% respectively. The water absorption of the lanolin before treatment was 180% and after treatment 155%. The addition of 1% by weight of stearyl alcohol to the treated lanolin increased the water absorption to 250%.

EXAMPLE 5

Using the same technique and lanolin as in Example 3 washing was carried out with 82% iso-propanol at 50° C. Reductions in free fatty alcohol content and detergent were as follows:

| | % free fatty alcs. | % Detergents |
|---|---|---|
| Original lanolin | 7.3 | 0.28 |
| washed with 10 volumes | 3.3 | 0.04 |
| Washed with 20 volumes | 2.6 | 0.01 |
| Washed with 30 volumes | 1.5 | 0.01 |

The lanolin after washing with 30 volumes of isopropanol had a water absorption of 140%. The addition of 1.5% of alcohol alcohol increased the water absorption to 240%.

EXAMPLE 6

100 g of Anhydrous Lanolin were washed 10 times at 55° C with 100 ml per wash using various polar solvents. The results were as follows:

| | % free fatty alcs. | % Detergent |
|---|---|---|
| Original lanolin | 12.5 | 0.25 |
| after 20 washes with 100% methanol | 2.8 | 0.01 |
| after 20 washes with 100% acetic acid | 1.8 | 0.03 |
| after 20 washes with 92% acetone | 2.9 | 0.03 |

EXAMPLE 7

Anhydrous Lanolin BP was washed using the technique described in Example 3. Subsequently the washed lanolin was passed through a molecular still using the technique described in Example 2. The results were as follows:

| | % free fatty alcs. | % Detergent |
|---|---|---|
| Original lanolin | 9.7 | 0.19 |
| after washing with 20 volumes of 95% IMS | 2.1 | 0.01 |
| after washing and molecular distillation | 1.1 | 0.01 |

EXAMPLE 8

15 g of Anhydrous Lanolin B.P. were dissolved in 85 ml of heptane and the solution washed 5 times at 15.5° C with 50 ml per time of n-propanol. After distilling off solvent, 12g of treated lanolin were recovered and the following results obtained:

| | % free fatty alcs. | % detergent |
|---|---|---|
| untreated lanolin | 12.0 | 0.26 |
| treated lanolin | 2.5 | 0.02 |

What I claim is:

1. A process for the production of hypoallergenic lanolin wherein lanolin is treated to reduce both the free fatty alcohol content to less than 3.0% and the detergent content to less than 0.05% while otherwise retaining the lanolin esters substantially chemically unchanged.

2. A process for the production of hypoallergenic lanolin as in claim 1 comprising the treatment of lanolin with vacuum at an absolute pressure of 20 to 150 millitorrs and a temperature of 180° C to 240° C.

3. A process for the production of hypoallergenic lanolin wherein lanolin is treated with a polar solvent under controlled conditions of pressure and temperature to simultaneously reduce the free fatty alcohol content to less than 3.0% and the detergent content to less than 0.05%, said polar solvent being a material or mixture of materials selected from the group consisting of methanol, ethanol, industrial methylated spirits, isopropanol, n-propanol, acetone and acetic acid.

4. A process as claimed in claim 3 in which the lanolin to be treated is dissolved in a substantially non-polar solvent selected from the group consisting of hexane, heptane and a hydrocarbon solvent of boiling range between 40° and 100° C.

5. A process according to claim 3 in which the temperature during treatment is from 40° to 80° C.

6. A process according to claim 3 in which the temperature during treatment is from 10° to 50° C.

* * * * *

UNITED STATES PATENT OFFICE

CERTIFICATE OF CORRECTION

Patent No. 4,091,035 Dated May 23, 1978

Inventor(s) Edward Watson Clark

It is certified that error appears in the above-identified patent and that said Letters Patent are hereby corrected as shown below:

Column 7, line 48, change "alcohol alcohol" to --cetyl alcohol--.

Signed and Sealed this

*Thirty-first* Day of *October 1978*

[SEAL]

*Attest:*

RUTH C. MASON
*Attesting Officer*

DONALD W. BANNER
*Commissioner of Patents and Trademarks*